United States Patent [19]

Bekhazi et al.

[11] Patent Number: 5,068,405
[45] Date of Patent: Nov. 26, 1991

[54] FAMOTIDINE INTERMEDIATES AND THEIR PREPARATION

[75] Inventors: Michel Bekhazi; Josef Oren, both of Quebec, Canada

[73] Assignee: Delmar Chemicals Inc., Quebec, Canada

[21] Appl. No.: 549,222

[22] Filed: Jul. 6, 1990

[51] Int. Cl.⁵ .................... C07C 307/00; C07C 53/10; C07C 309/04; C07C 309/30
[52] U.S. Cl. ......................... 562/83; 562/86; 562/114; 562/602; 562/605; 564/79
[58] Field of Search .................... 562/114, 83, 86, 602, 562/605; 564/79

[56] References Cited

U.S. PATENT DOCUMENTS

| | | | |
|---|---|---|---|
| 3,121,084 | 2/1964 | Winberg | 564/79 |
| 4,675,134 | 6/1987 | Miura et al. | 562/86 |
| 4,731,479 | 3/1988 | Bod et al. | 564/79 |

*Primary Examiner*—Glennon H. Hollrah
*Assistant Examiner*—Susan Treanor
*Attorney, Agent, or Firm*—Wyatt, Gerber, Burke & Badie

[57] ABSTRACT

Halogenated N-sulfamyl propionamidine addition salts corresponding to the formula

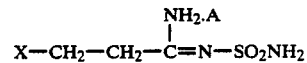

are provided, in which X represents halogen and A represents an acid selected from sulfuric acid, nitric acid, benzenesulfonic acid; toluenesulfonic acid; 2,4,5-trichlorobenzenesulfonic acid; trichloroacetic acid; trifluoroacetic acid or methanesulfonic acid. They are useful as intermediates in the preparation of famotidine. They are prepared by reacting a halogenated propionitrile with the respective acid.

7 Claims, No Drawings

FAMOTIDINE INTERMEDIATES AND THEIR PREPARATION

This invention relates to propionamidine derivatives and processes for their preparation and use. More particularly, it relates to halogenated N-sulfamyl propionamidine addition salts, their preparation and use in preparation of famotidine.

Famotidine, a full chemical name of which is N-sulfamyl-3-(2-guanidino-thiazol-4-yl-methylthio)-propionamidine, also known as 3-[[[2-[(aminoiminomethyl)amino]-4-thiazolyl]methyl]thio]-N-(aminosulfonyl)propanimidamide, of formula I:

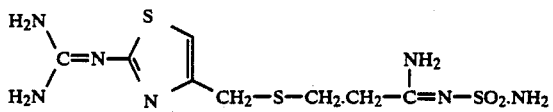

has pharmaceutical use as an anti-ulcer agent, in the treatment of gastric and intestinal ulcers. In U.S. Pat. No. 4,731,479 (Bod et al), a process for the preparation of famotidine is disclosed, in which a halogen-substituted propionamidine acid addition salt of formula II

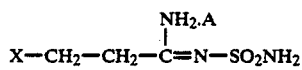

in which X represents halogen is prepared by reaction of a 3-halopropionitrile with sulfamide, in the presence of a hydrogen halide HX, i.e. hydrogen chloride, hydrogen bromide or hydrogen iodide. The halogen-substituted propionamidine acid addition salt so formed is then reacted with S-(2-guanidino-thiazol-4-yl-methyl-)isothiourea, to prepare famotidine.

The use of hydrogen halide acids in the process for preparing the propionamidines of Formula II does however present certain drawbacks. As described in the aforementioned Bod et al patent, the hydrogen halide gases are passed through a solution of the reagents for 1 to 100 hours. In the specific examples, times of at least 3 hours are used. This can result in large wastage of acid. The hydrogen halides have a very high volatility at the preferred reaction temperatures, leading to excessive use and wastage of acid, danger to personnel, a requirement for purification of effluent gases and excessive corrosion of equipment.

When hydrogen chloride is used, as is preferred according to the specific examples of the aforementioned Bod et al patent, its presence in the reaction mixture makes the suspension extremely hygroscopic, corrosive and hard to handle. Moreover, during the reaction, the suspension becomes much more viscous, so that stirring becomes difficult and in some instances, sulfamide may remain unreacted. Because the hydrogen chloride addition is continued throughout the reaction time, the mother liquors become supersaturated with hydrogen chloride, so that degassing becomes necessary before any suction filtration can be undertaken.

Thus it is an object of the present invention to provide a novel process for preparing halogenated propionamidine acid addition salts, which avoids the use of hydrogen halide acids such as hydrogen chloride.

According to the present invention, from one aspect, there is provided a process for preparing halogenated N-sulfamyl propionamidine addition salts corresponding to the formula III

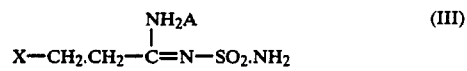

in which X represents halogen and A represents an acid selected from sulfuric acid; nitric acid; benzenesulfonic acid; toluenesulfonic acid; 2,4,5-trichlorobenzenesulfonic acid; trichloroacetic acid; trifluoroacetic acid and methanesulfonic acid, which comprises reacting a halogenated propionitrile of formula $X-CH_2-CH_2-CN$ with sulfamide in the presence of an acid selected from sulfuric acid, nitric acid, benzenesulfonic acid, toluenesulfonic acid, trichlorobenzenesulfonic acid, trichloroacetic acid, trifluoroacetic acid and methanesulfonic acid.

The use of one or more of the selected acids, to produce the respective acid addition salts of the propionamidine, avoids the problems encountered with the use of hydrogen halide acids such as hydrogen chloride. The selected acids are solids or liquids, and thus are easier to handle, pose fewer environmental problems, and are less corrosive of equipment than gaseous HCl. Moreover, the amount of acid can be weighed accurately, and its concentration easily controlled.

Moreover, the use of one or other of the selected acids allows maximum yields of the propionamidine salt to be produced by employing much smaller relative quantities of the acid. Thus it has been found that the yield is maximized by the use of just two moles of acid per mole of sulfamide. Increases in the relative proportions of the selected acid, e.g. to 4–6 moles per mole of sulfamide, gives lower yields. This is to be contrasted with the prior art HCl use, where acid addition continues throughout the reaction period, with consequent reagent wastage, purification problems and the other problems referred to above.

The halogenated N-sulfamyl propionamidine addition salts of formula III given above are novel, and form a further aspect of this invention. Unlike the hydrogen halide addition salts, the addition salts of formula III are typically slightly soluble in 3-chloropropionitrile, the preferred starting material, so that little if any viscosity change in the reaction mixture takes place during reaction. The isolation of the products is simple and straightforward, due to the nature and filterability of the salts. The starting materials are relatively inexpensive, and available on an industrial scale. After neutralization with a base, the unreacted nitriles can be recovered by distillation.

The process of the present invention is typically conducted by adding the acid to the halonitrile, and then adding the sulfamide under agitation. The temperature is adjusted to the desired level, normally 5° C.–80° C. and preferably 40° C.–60° C., and the reaction proceeds for a period of 5–240 hours, typically 8–16 hours. When the reaction is complete, the suspension is diluted with an inert solvent and filtered. The solid product may be purified by resuspension in a suitable organic solvent, followed by filtration and drying. Suitable inert solvents to effect dilution include methylene chloride and diethyl ether. For further purification by resuspension, acetone is a suitable solvent.

The molar ratios of the reactants, per mole of sulfamide, is preferably from 2.5–8.0 moles of halonitrile (most preferably 6.0 moles), and 1.5-5.0 moles of acid (most preferably 2.0 moles). Excess halonitrile can usually be recovered as described.

All the acid addition salts of the present invention show IR bands at $cm^{-1} = 1675$ (C=N) and 1160 (SO$_2$). When chloro is used as group X in the formula III, as is usual and preferred, they show an IR band at $cm^{-1} = 650$ (C-Cl).

The acid addition salts of the present invention can be readily used for preparation of famotidine, by reaction with S-(2-guanidino-thiazol-4-yl-methyl)-isothiourea, by known procedures.

The invention is further described in the following illustrative example.

EXAMPLE 1

N-Sulfamyl-3-chloropropionamidine methanesulfonic acid addition salt

Sulfamide (9.6 g, 0.1 mole) was added to a solution of methanesulfonic acid anhydrous (19.2 g, 0.2 mole) in 3-chloropropionitrile (51.3 g, 0.6 mole). The suspension was heated at 55-60° C., for 18 hours. At the end of the heating period, the mixture was cooled to room temperature, diluted with methylene chloride (150 ml), and filtered. The solid, thus obtained, was suspended in acetone (50 ml), and the suspension filtered and the product dried, to yield about 19 g of product.

When this example was repeated at 20-25° C. reaction temperature, 9.7 g of product was obtained. When the example was repeated at 5-10° C., 6.1 g of product was obtained.

EXAMPLE 2

N-Sulfamyl-3-chloropropionamidine methanesulfonic acid addition salt

Sulfamide (9.6 g, 0.1 mole) was added to a solution of methanesulfonic acid anhydrous (38.4 g, 0.4 mole) in 3-chloropropionitrile (51.3 g, 0.6 mole). The suspension was heated at 55-60° C., for 18 hours. At the end of the reacting period, the mixture was diluted with methylene chloride (150 ml) and filtered. The solid, thus obtained, was suspended in acetone (50 ml), and the suspension filtered and the product dried, to yield 16.35 g of product.

EXAMPLE 3

N-Sulfamyl-3-chloropropionamidine methanesulfonic acid addition salt

Sulfamide (9.6 g, 0.1 mole) was added to a solution of methanesulfonic acid anhydrous (48.0 g, 0.5 mole) in 3-chloropropionitrile (51.3 g, 0.6 mole). The suspension was heated at 55-60° C., for 18 hours. At the end of the reacting period, the mixture was diluted with methylene chloride (150 ml), and filtered. The solid, thus obtained, was suspended in acetone (50 ml), and the suspension filtered and the product dried, to yield 13.3 g of product.

EXAMPLE 4

N-Sulfamyl-3-chloropropionamidine p-toluenesulfonic acid addition salt

Sulfamide (9.6 g, 0.1 mole) was added to a suspension of p-toluenesulfonic acid monohydrate (38.0 g, 0.2 mole) in 3-chloropropionitrile (51.3 g, 0.6 mole). The suspension was heated at 55-60° C., for 18 hours. At the end of the heating period, the mixture was cooled to room temperature, diluted with methylene chloride (150 ml), and filtered. The solid, thus obtained, was suspended in acetone (50 ml) and the suspension filtered and the product dried.

Yield: 21.2 g (60%).

M.P.: 222.5-226° C. (decomposes).

NMR (ppm) (D$_2$O): 7.86 (d, 2H; j=8Hz); 7.35 (d, 2H; J=8Hz); 3.60 (t, 2H, J=6Hz); 2.62 (d, 2H; J=6Hz); 2.33 (s, 3H).

EXAMPLE 5

N-Sulfamyl-3-chloropropionamidine benzenesulfonic addition salt

Sulfamide (9.6 g, 0.1 mole) was added to a suspension of benzenesulfonic acid (31.6 g, 0.2 mole) in 3-chloropropionitrile (51.3 g, 0.6 mole). The suspension was heated at 55-60° C., for 18 hours. At the end of the heating period, the mixture was cooled to room temperature, diluted with methylene chloride (150 ml), and filtered. The solid, thus obtained, was suspended in acetone (50 ml), and the suspension filtered and the product dried.

Yield: 17.0 g (51%),

M.P.: 163-169.5° C. (decomposes),

NMR (ppm)(D$_2$O): 8.6-7.2 (m, 5H); 3.66 (d, 2; J=6Hz); 2.50 (d, 2H; J=6H).

EXAMPLE 6

N-Sulfamyl-3-chloropropionamidine 2,4,5-trichlorobenzene sulfonic acid addition salt Sulfamide (9.6 g, 0.1 mole) was added to a solution of 2,4,6-trichlorobenzenesulfonic acid (52.2 g, 0.2 mole) in 3-chloropropionitrile (51.3 g, 0.6 mole). The suspension was heated at 55-60° C., for 18 hours. At the end of the heating period, the mixture was cooled to room temperature, diluted with methylene chloride (150 ml), and filtered. The solid, thus obtained, was suspended in acetone (50 ml) and the suspension filtered and the product dried.

Yield: 26.7 g (60.3%),

M.P.: 151.5-154° C. (decomposes),

NMR (ppm) (D$_2$O/DMSO-d$_6$): 7.99 (s, 1H); 7.76 (s, 1H); 3.76 (d, 2H; J=6Hz); 2.66 (d, 2H; J=6Hz).

EXAMPLE 7

N-Sulfamyl-3-chloropropionamidine sulfuric acid addition salt

Sulfamide (9.6 g, 0.1 mole) was added to a solution of conc. sulfuric acid (98%, 9.8 g, 0.1 mole) in 3-chloropropionitrile (51.3 g, 0.6 mole). The suspension was heated at 55-60° C., for 18 hours. At the end of the heating period, the mixture was cooled to room temperature, diluted with methylene chloride (150 ml), and filtered. The solid, thus obtained, was suspended in acetone (50 ml), and the suspension filtered and the product dried.

Yield: 15.4 g (54%),

M.P.: 195.5-200 200° C. (decomposes),

NMR (ppm) (D$_2$O/DMSO-d$_6$) 3.76 (d, 2H; J=6Hz); 2.76 (d, 2H; J=6Hz).

EXAMPLE 8

N-Sulfamyl-3-chloropropionamidine nitric acid addition salt

Sulfamide (9.6 g, 0.1 mole) was added to a solution of conc. nitric acid (12.6 g, 0.2 mole) in 3-chloropropionitrile (51.3 g, 0.6 mole). The suspension was heated at 55°-60° C., for 18 hours. At the end of the heating period, the dark mixture was cooled to room temperature, diluted with methylene chloride (150 ml), and filtered. The solid, thus obtained, was suspended in acetone (50 ml), and the suspension filtered and the product dried.

Yield: 6.0 g (25%).

M.P. 258° C. (decomposes).

We claim:

1. Halogenated N-sulfamyl propionamidine addition salts of the formula:

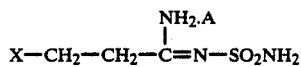

in which X represents halogen and A represents an acid selected from sufuric acid; nitric acid; benzenesulfonic acid; toluenesulfonic acid; 2,4,5-trichlorobenzenesulfonic acid; trichloroacetic acid; trifluoroacetic acid; and methanesulfonic acid.

2. N-sulfamyl-3-chloropropionamidine methanesulfonic acid.

3. N-sulfamyl-3-chloropropionamidine p-toluenesulfonic acid.

4. N-sulfamyl-3-chloropropionamidine benzensulfonic acid.

5. N-sulfamyl-3-chloropropionamidine 2,4,5-trichlorobenzenesulfonic acid.

6. N-sulfamyl-3-chloropropionamidine sulfuric acid.

7. N-sulfamyl-3-chloropropionamidine nitric acid.

* * * * *